United States Patent
Lee et al.

(10) Patent No.: US 12,337,042 B2
(45) Date of Patent: **\*Jun. 24, 2025**

(54) STRUCTURAL OPTIMIZATION METHOD TO IMPROVE THE THERANOSTIC PERFORMANCE OF PEPTIDE RECEPTOR-TARGETED RADIONUCLIDE THERAPY FOR CANCERS

(71) Applicant: University of Iowa Research Foundation, Iowa City, IA (US)

(72) Inventors: Dongyoul Lee, Iowa City, IA (US); Michael K. Schultz, Iowa City, IA (US); Mengshi Li, Iowa City, IA (US); Nicholas Baumhover, Iowa City, IA (US); F. Christopher Pigge, Iowa City, IA (US)

(73) Assignee: UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/771,562

(22) Filed: Jul. 12, 2024

(65) Prior Publication Data

US 2024/0366816 A1 Nov. 7, 2024

Related U.S. Application Data

(63) Continuation of application No. 17/795,792, filed as application No. PCT/US2021/015389 on Jan. 28, 2021.

(60) Provisional application No. 62/967,497, filed on Jan. 29, 2020.

(51) Int. Cl.
*A61K 51/10* (2006.01)
*A61K 51/08* (2006.01)
*A61P 35/00* (2006.01)

(52) U.S. Cl.
CPC ........ *A61K 51/1096* (2013.01); *A61K 51/088* (2013.01); *A61K 51/1036* (2013.01); *A61P 35/00* (2018.01)

(58) Field of Classification Search
CPC .............. A61K 51/1096; A61K 51/088; A61K 51/1036; A61K 51/0482; A61P 35/00
USPC ........................................................ 424/1.53
See application file for complete search history.

(56) References Cited

U.S. PATENT DOCUMENTS

| 5,310,535 | A | 5/1994 | Kruper et al. | |
| 11,179,484 | B2 * | 11/2021 | Schultz | A61K 47/64 |
| 11,576,987 | B2 * | 2/2023 | Schultz | A61K 51/0482 |
| 2023/0105344 | A1 | 4/2023 | Lee et al. | |

FOREIGN PATENT DOCUMENTS

| CN | 106084005 A | 11/2016 | | |
| WO | 2013029616 A1 | 3/2013 | | |
| WO | WO-2017223565 A1 * | 12/2017 | .......... | A61K 31/167 |
| WO | 2018132751 A1 | 7/2018 | | |
| WO | 2019240884 A2 | 12/2019 | | |

OTHER PUBLICATIONS

Delpassand, E , et al., "First clinical experience using targeted alpha-emitter therapy with 212Pb-Dotamtate (AlphaMedix TM) in patients with SSTR(+) neuroendocrine tumors", J Nucl Med 60, (Supplemental 1) Abstract 559 , 4 pages (2019).
Kratochwil, C , et al., "213Bi-Dotatoc receptor-targeted alpha-radionuclide therapy induces remission in neuroendocrine tumours refractory to beta radiation: a first-in-human experience", Eur J Nucl Med Mol Imaging 41, 2106-2119 (2014).
Lee, D , et al., "Dosimetry and Potential Toxicities of 212Pb-Dotatoc in a Preclinical Model: Towards Personalized Dosimetry Based Alpha-Particle Therapy for Neuroendocrine Tumors", Pancreas Journal 49(3), Abstracts, p. 475 (2020).
Li, M , et al., "Automated cassette-based production of high specific activity peptide-based theranostic radiopharmaceuticals for image-guided radionuclide therapy for cancer", Applied Radiation and Isotopes 127, 52-60 (2017).
Patent Cooperation Treaty , International Search Report and Written Opinion for PCT/US2021/015389, 17 pages, dated May 3, 2021.
Stallons, T , et al., "Preclinical Investigation of 212Pb-Dotamtate for Peptide Receptor Radionuclide Therapy in a Neuroendocrine Tumor Model", Molecular Cancer Therapies 18(5), 1012-1021 (2019).
Tworowska, I , et al., "Image guided therapy of SSTR(+)-neuroendocrine tumors (NETs) using 203Pb octreotate analog", Journal of Nuclear Medicine 59 (Supplement 1), Abstract 1124, 3 pages (2018).
Lee, D, "Enhancing the Therapeutic Efficacy of Peptide Receptor Radionuclide Therapy for Neuroendocrine Tumors", The University of Iowa, Thesis Dissertation, 24 pages (2020).

(Continued)

*Primary Examiner* — Michael G. Hartley
*Assistant Examiner* — Sean R Donohue
(74) *Attorney, Agent, or Firm* — Viksnins Harris Padys Malen LLP

(57) ABSTRACT

The present invention provides in certain embodiments a carcinoma-targeting conjugate comprising Formula I:

T-L-X wherein T is a SSTR2 targeting ligand,

L is a linker, and

X is a chelator, for the therapeutic treatment of cancer, and methods of use thereof.

4 Claims, 12 Drawing Sheets

(56) References Cited

OTHER PUBLICATIONS

Li, M, "Melanocortin subtype 1 receptor (MC1R) targeted-radionuclide therapy for melanoma", The University of Iowa, Thesis Dissertation, 111 pages (2018).
Saidi, et al., "Side-by-Side Comparison of the In Vivo Performance of [212Pb]Pb-Dotamtate and Other SSTR2-Targeting Compounds", Journal of Nuclear Medicine, doi:10.2967/jnumed.124.268345, 7 pages (2025).
Wahl, et al., "Interim Safety and Efficacy Data of [212Pb]VMT-α-NET in Somatostatin Receptor 2 (SSTR2) Expressing Neuroendocrine Tumors (NETs) (NCT05636618)", American Society of Clinical Oncology (ASCO) Gastrointestinal Tumors Symposium held in San Francisco, 1 page (2025).
Antunes, P, et al., "Influence of different spacers on the biological profile of a DOTA-somatostatin analogue", Bioconjug Chem 18, 84-92 (2007).
Benesova, M, et al., "Preclinical Evaluation of a Tailor-Made DOTA-Conjugated PSMA Inhibitor with Optimized Linker Moiety for Imaging and Endoradiotherapy of Prostate Cancer", J Nucl Med 56, 914-920 (2015).
Brabander, T, et al., "Long-Term Efficacy, Survival, and Safety of [177Lu-DOTA0,Tyr3]octreotide in Patients with Gastroenteropancreatic and Bronchial Neuroendocrine Tumors", Clin Cancer Res 23 (16), 4617-4624 (2017).
Cai, Z, et al., "64Cu-labeled somatostatin analogues conjugated with cross-bridged phosphonate-based chelators via strain-promoted click chemistry for PET imaging: in silico through in vivo studies", J Med Chem 57 (14), 6019-6029 (2014).
Chappell, L., et al., "Synthesis, characterization, and evaluation of a novel bifunctional chelating agent for the lead isotopes 203Pb and 212Pb", Nucl. Med. Biol 27, 93-100 (2000).
Chen, J, et al., "Evaluation of an 111In-DOTA-Rhenium Cyclized a-MSH Analog: A Novel Cyclic-Peptide Analog with Improved Tumor-Targeting Properties", J Nucl Med 42, 1847-1855 (2001).
Dasari, A, et al., "Trends in the Incidence, Prevalence, and Survival Outcomes in Patients With Neuroendocrine Tumors in the United States", JAMA Oncol 3 (10), 1335-1342 (2017).
De Blois, E, et al., "Iodination and Stability of Somatostatin Analogues: Comparison of Iodination Techniques. A Practical Overview", Current Topics in Medicinal Chemistry 12, 9 pages (2012).
Dos Santos, J, et al., "Development and dosimetry of 203Pb/212Pb-labelled PSMA ligands: bringing Bthe leadinto PSMA-targeted alpha therapy?", European Journal of Nuclear Medicine and Molecular Imaging 46, 1081-1091 (2019).
FDA, "FDA Approves Lutathera for GEP NET Therapy", U.S. Food and Drug Administration Advanced Accelerator Applications/Novartis National Institutes of Health, Newsline, Journal of Nuclear Medicine 59 (4), 9N (2018).
Gape, P, et al., "Towards Effective Targeted Alpha Therapy for Neuroendocrine Tumours: A Review", Pharmaceuticals 17, 334, 26 pages (2024).
Gourni, E, et al., "N-Terminal Modifications Improve the Receptor Affinity and Pharmacokinetics of Radiolabeled Peptidic Gastrin-Releasing Peptide Receptor Antagonists: Examples of 68Ga- and 64Cu-Labeled Peptides for PET Imaging", J Nucl Med 55, 1719-1725 (2014).
Guo, H, et al., "Introduction of an 8-Aminooctanoic Acid Linker Enhances Uptake of 99mTc-Labeled Lactam Bridge—Cyclized a-MSH Peptide in Melanoma", Journal of Nuclear Medicine 55 (12), 2057-2063 (2014).
Imhof, A, et al., "Response, Survival, and Long-Term Toxicity After Therapy With the Radiolabeled Somatostatin Analogue [90Y-DOTA]-TOC in Metastasized Neuroendocrine Cancers", Journal of Clinical Oncology 29 (17), 2416-2423 (2011).
Kaemmerer, D, et al., "Inverse expression of somatostatin and CXCR4 chemokine receptors in gastroenteropancreatic neuroendocrine neoplasms of different malignancy", Oncotarget 5 (29), 27566-27579 (2015).
Kratochwil, C., et al., "213Bi-Dotatoc receptor-targeted alpha-radionuclide therapy induces remission in neuroendocrine tumours refractory to beta radiation: a first-in-human experience", Eur J Nucl Med Mol Imaging, DOI 10.1007/s00259-014-2857-9, 16 pages (2014).
Kratochwil, C, et al., "225Ac-PSMA-617 for PSMA-Targeted a-Radiation Therapy of Metastatic Castration-Resistant Prostate Cancer", The Journal of Nuclear Medicine 57 (12), 1941-1944 (2016).
Kwekkeboom, D, et al., "Treatment With the Radiolabeled Somatostatin Analog [177Lu-DOTA0,Tyr3]Octreotate: Toxicity, Efficacy, and Survival", Journal of Clinical Oncology 26 (13), 2124-2130 (2008).
Lee, D, et al., "Modeling Cell and Tumor-Metastasis Dosimetry with the Particle and Heavy Ion Transport Code System (PHITS) Software for Targeted Alpha-Particle Radionuclide Therapy", Radiat Res 190 (3), 236-247 (2018).
Lee, D, et al., "Structural modifications toward improved lead-203/lead-212 peptide-based image-guided alpha-particle radiopharmaceutical therapies for neuroendocrine tumors", European Journal of Nuclear Medicine and Molecular Imaging 51, 1147-1162 (2024).
Li, M, et al., "Enhancing the Efficacy of Melanocortin 1 Receptor-Targeted Radiotherapy by Pharmacologically Upregulating the Receptor in Metastatic Melanoma", Mol Pharm 16 (9), 3904-3915 (2019).
Li, M, et al., "Preclinical Evaluation of a Lead Specific Chelator (PSC) Conjugated to Radiopeptides for 203Pb and 212Pb-Based Theranostics", Pharmaceutics 15, 414, 17 pages (2023).
Lin, M, et al., "Effects of Chelator Modifications on 68Ga-Labeled [Tyr3]Octreotide Conjugates", Mol Imaging Biol 15(5), 606-613 (2013).
Ma, M, et al., "Rapid kit-based (68)Ga-labelling and PET imaging with THP-Tyr(3)-octreotate: a preliminary comparison with DOTA-Tyr(3)-octreotate", EJNMMI Res 5(1), 52, 1-11 (2015).
Marincek, N, et al., "Somatostatin-based radiotherapy with [90Y-DOTA]-TOC in neuroendocrine tumors: long-term outcome of a phase I dose escalation study", Journal of Translational Medicine 11 (17), 11 pages (2013).
Martin, M, et al., ""Click" cyclized gallium-68 labeled peptides for molecular imaging and therapy: Synthesis and preliminary in vitro and in vivo evaluation in a melanoma model system", Recent Results Cancer Res 194, 149-175 (2013).
Oronsky, B, et al., "Nothing but Net: A Review of Neuroendocrine Tumors and Carcinomas", Neoplasia 19 (12), 991-1002 (2017).
Pretze, M, et al., "Influence of the Molar Activity of 203/212Pb-PSC-PEG2-TOC on Somatostatin Receptor Type 2-Binding and Cell Uptake", Pharmaceuticals 16, 1605, 11 pages (2023).
Schweinsberg, C, et al., "Novel Glycated [99mTc(CO)3]-Labeled Bombesin Analogues for Improved Targeting of Gastrin-Releasing Peptide Receptor-Positive Tumors", Bioconjugate Chem 19, 2432-2439 (2008).
Sgouros, G, et al., "MIRD Pamphlet No. 22 (Abridged): Radiobiology and Dosimetry of a-Particle Emitters for Targeted Radionuclide Therapy*", J Nucl Med 51, 311-328 (2010).
Strosberg, J, et al., "Phase 3 Trial of 177Lu-Dotatate for Midgut Neuroendocrine Tumors", N Engl J Med 376, 125-135 (2017).
Tornesello, A, et al., "New Insights in the Design of Bioactive Peptides and Chelating Agents for Imaging and Therapy in Oncology", Molecules 22, 1282, 21 pages (2017).
Michler, et al., "[203/212Pb]Pb-VMT-α-NET as a novel theranostic agent for targeted alpha radiotherapy—first clinical experience", European Journal of Nuclear Medicine and Molecular Imaging, https://doi.org/10.1007/s00259-025-07269-0, 13 pages (2025).

* cited by examiner

A

DOTATOC

B

PSCTOC

C

PSC-PEG₂/PEG₄-TOC

FIGURES 6A-6C
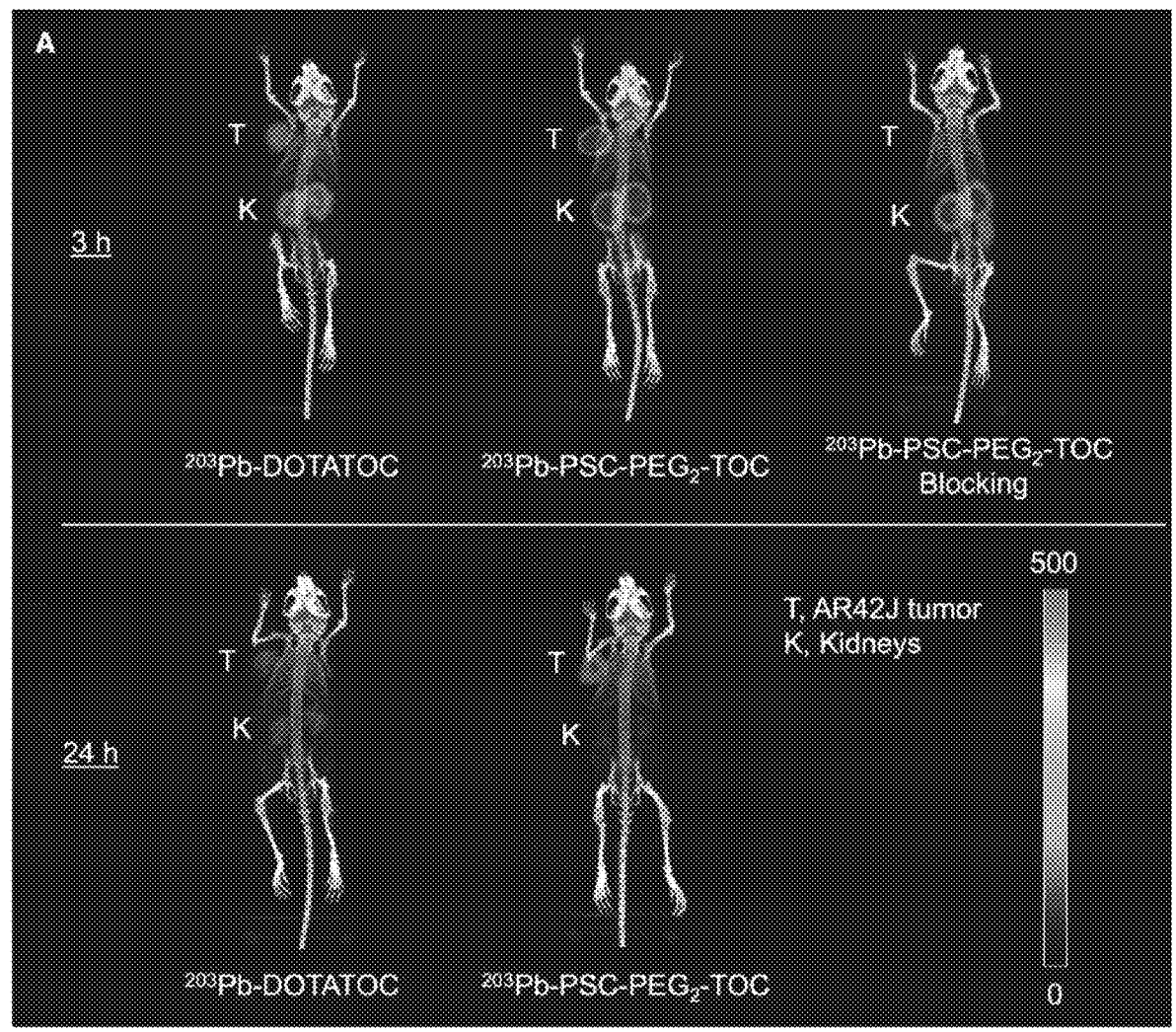
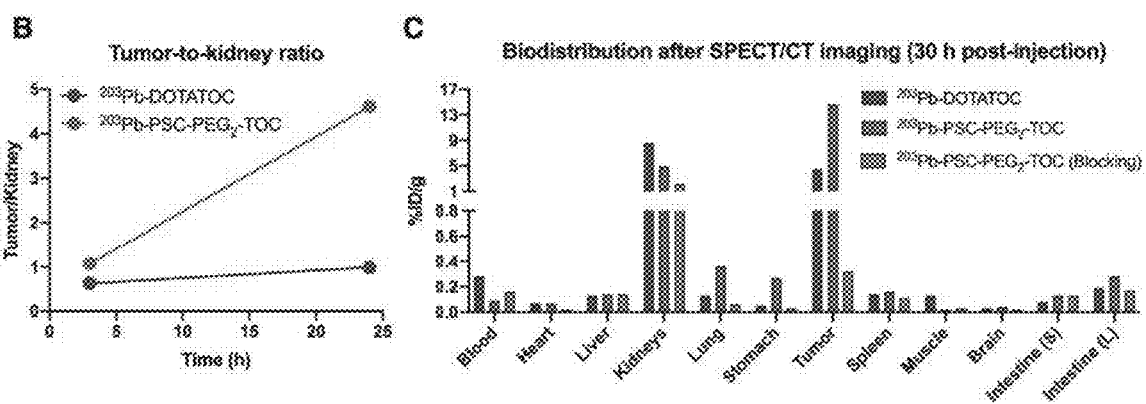

STRUCTURAL OPTIMIZATION METHOD TO IMPROVE THE THERANOSTIC PERFORMANCE OF PEPTIDE RECEPTOR-TARGETED RADIONUCLIDE THERAPY FOR CANCERS

CROSS-REFERENCE TO RELATED APPLICATIONS

This application is a Continuation application of U.S. patent application Ser. No. 17/795,792, filed on Jul. 27, 2022, which claims benefit under 35 U.S.C. § 371 to Patent Cooperation Treaty Application Number PCT/US2021/015389, filed on Jan. 28, 2021, which claims priority to U.S. Provisional Patent Application Ser. No. 62/967,497, filed on Jan. 29, 2020, the disclosure of which are hereby incorporated herein by reference in their entirety.

STATEMENT REGARDING FEDERALLY SPONSORED RESEARCH

This invention was made with government support under R01 CA243014 and P50 CA 174521 awarded by the National Institutes of Health. The government has certain rights in the invention.

BACKGROUND OF THE INVENTION

Neuroendocrine neoplasms (NENs) are a heterogeneous group of neoplasm, the incidence of which has been constantly increasing over the decades (1,2). NENs are commonly subcategorized into well-differentiated (low to intermediate grade) neuroendocrine tumors (NETs) and poorly-differentiated (high grade) neuroendocrine carcinomas (NECs) by histological, biological, and pathological differences (2,3). In many cases, the well-differentiated NETs are less aggressive than the poorly-differentiated NECs, and they respond to several targeted forms of therapies (2). The majority (>80%) of NENs express somatostatin receptors (3), and among them, somatostatin receptor subtype 2 (SSTR2) is a well-known target for a specific therapy called peptide receptor radionuclide therapy (PRRT). The current developments of the SSTR2-targeted PRRT are based on beta-particle emitters, Yttrium-90 ($^{90}$Y) and Lutetium-177 ($^{177}$Lu) (4-8). Especially, $^{177}$Lu-labeled DOTA-tyr$^3$-octreotate ($^{177}$Lu-DOTATATE; Lutathera) is the only US Food and Drug Administration (FDA)-approved radiotherapeutic drug for the well-differentiated NETs (9). The drug had shown a therapeutic benefit by tumor response and increased progression-free survival (PFS) of the patients (6-8). However, the benefit was limited to partial response—and complete responses are rarely reported.

Alpha-particle emitters are alternatives to the conventional beta-particle emitters bringing significantly higher radiation doses (up to a few hundred fold) in cells and tumor metastases from decays (10) as well as higher relative biological effectiveness (RBE) arising from the high linear energy transfers (LETs) of the alpha particles (11). Multiple studies demonstrated that the alpha-particle emitters have the promise to treat the cancer patients who were refractory to the beta-particle emitters (12,13). Lead-212 ($^{212}$Pb) is an attractive alpha-particle emitter that has a favorable half-life (10.64 h) for clinical application (14) and is well-matched with the biological half-lives (few hours) of peptides in vivo. Also, $^{212}$Pb has the diagnostic pair, lead-203 ($^{203}$Pb), which is available for single-photon emission computed tomography (SPECT) by 279 keV photons (81% intensity) (15). The half-life (51.87 h) of $^{203}$Pb is long enough to monitor the biodistribution and pharmacokinetics of each patient by serial imaging up to 4-5 half-lives of $^{212}$Pb (14). In addition, the theranostic pair shares the same chemistry for radiolabeling, and has a similar binding affinity and pharmacokinetics when labeled with the same peptides, which is critical for precise dosimetry.

Changes in peptide structure can shift the binding affinity, pharmacokinetics, and biodistribution of radiopeptides significantly. Thus, structural changes to the peptide can potentially improve therapeutic outcomes of the peptide-based therapies, by improving on these parameters. Approaches to manipulation of the ultimate performance of peptides for this application include modifications to the cyclization method, insertion of appropriate size and composition of the linker that connects the chelator to the peptide backbone, and development of radionuclide-specific chelators. Rhenium-coordinated peptide cyclization (16) and "click"-cyclization as well as a further optimization with glycine-glycine (GG) linker (17) have been evaluated in melanoma models targeting melanocortin receptor subtype 1 (MC1R), suggesting the potential of improved tumor targeting and pharmacokinetics and biodistribution by the approaches. Many other investigations implicated that radiopeptides can be optimized for optimal tumor targeting with improved in vivo performance by different linker insertions (17-19) and chelator modifications (20-22).

In this study, modifications in peptide structure with various strategies were made based on Tyr$^3$-octreotide (TOC). A new chelator composition, 1,4,7,10-tetraazacyclododecane-7-acetamide-1,4,10-triacetic acid (herein, called Pb-specific chelator or PSC) was introduced for Pb isotopes and other 2+ charged radionuclides. The structure was further optimized with the additions of polyethylene glycol (PEG) linkers between the chelator and TOC. DOTA-TOC, PSCTOC, PSC-PEG$_2$-TOC, and PSC-PEG$_4$-TOC were synthesized by the standard Fmoc-based solid phase peptide synthesis. The performance of each peptide was evaluated comprehensively by radiolabeling efficiency, binding affinity, cellular uptake, and biodistribution, and the lead compound was used for $^{203}$Pb SPECT imaging and $^{212}$Pb therapy/toxicity studies.

SUMMARY OF THE INVENTION

As noted above, the present invention is directed to a new chelator which, in one embodiment, is 1,4,7,10-tetraazacyclododecane-7-acetamide-1,4,10-triacetic acid. The chelator is specific to 2+ charged radionuclides, including Pb isotopes. The structure includes a polyether linker between the chelator and Tyr$^3$-octreotide (TOC) or other peptide, with a polyethylene glycol (PEG) linker being preferred. The invention is primarily used to target any cancers that express the somatostatin receptor subtype 2 (SSTR2) which include, but are not limited to, neuroendocrine tumors, small cell lung cancer, meningioma, neuroblastoma, medulloblastoma, paraganglioma, and pheochromacytoma.

DETAILED DESCRIPTION OF THE INVENTION

The present invention provides in certain embodiments a carcinoma-targeting conjugate comprising Formula I:

T-L-X wherein T is a SST2R targeting ligand,
L is a linker, and
X is a chelator.
for the therapeutic treatment of cancer.

In certain embodiments, the radiolabeled SST2R-targeted ligand is a peptide, or antibody or antibody fragment, or a small molecule.

In certain embodiments. T is Tyr$^3$-octreotide.

In certain embodiments, the SST2R-targeted ligand is radiolabeled with a radionuclide that is chemically bound to the chelator (X) and used for medical imaging and/or therapy of the cancerous tumors.

In certain embodiments, the radionuclide is Ga-68; In-111; Pb-203; F-18; C-11; Zr-89; Sc-44; Tc-99m or other medical radionuclide used for imaging.

In certain embodiments, the radionuclide is Y-90; Pb-212; Bi-212; Bi-213; At-211; Lu-177; Re-188; or other medical radionuclide used to treat the cancerous tumors.

In certain embodiments, L is a chemical linker that is inserted into a position between the peptide backbone that recognizes the SST2R protein and the chelator that is used to radiolabel the composition using radionuclides for therapy and/or diagnostic imaging; and the linker improves the binding and/or internalization of the composition into cells; improves the retention of the composition in tumors; and improves the clearance of residual composition through other excretion pathways for more precise delivery of radiation to the cancerous tissue, while minimizing radiation exposure to other organs (for example, kidneys).

In certain embodiments, L is a polyether linker comprising up to 4 carbons consisting of an aliphatic carbon chain that connects the chelator to the peptide backbone.

In certain embodiments, L is $PEG_n$, wherein n is 1-4. In certain embodiments, n is 2 or 4.

In certain embodiments, X is radiolabeled with a radionuclide that is used for medical imaging and/or therapy of the cancerous tumors.

In certain embodiments, the radionuclide is Ga-68; In-111; Pb-203, Cu-64 or other Cu isotopes; F-18; C-11; Zr-89; Sc-44; Tc-99m or other medical radionuclide used for imaging.

In certain embodiments, the radionuclide is Y-90; Pb-212; Cu-67; or other Cu isotopes; Bi-212; Bi-213; At-211; Lu-177; Re-188; or other medical radionuclide used to treat the cancerous tumors.

In certain embodiments, the chelating agent is based on 1,4,7,10-tetraazacyclododecane-7-acetamide-1,4,10-triacetic acid or other chelator that is used to bind the radionuclide for diagnostic imaging or therapy for cancer or other disease.

The present invention provides in certain embodiments a conjugate consisting of PSC-PEG$_2$/PEG$_4$-TOC.

In certain embodiments, the agent is administered orally or parenterally.

In certain embodiments, the agent is administered subcutaneously.

In certain embodiments, the conjugate is administered orally or parenterally.

In certain embodiments, the method further comprises administering an anti-cancer composition.

In certain embodiments, the conjugate is administered in a single dose.

In certain embodiments, the conjugate is administered in multiple doses.

In certain embodiments, the conjugate is administered sequentially daily for several days.

In certain embodiments, the conjugate is administered once per week for 1 month. In certain embodiments, the conjugate is administered once per week for up to 6 months.

In certain embodiments, the conjugate is administered in a dose of 1 mCi for medical imaging.

In certain embodiments, the conjugate is administered in a dose of up to 10 mCi for medical imaging.

In certain embodiments, the conjugate is administered in a dose of up to 50 mCi for medical imaging.

In certain embodiments, the conjugate is administered in a dose of 0.1 mCi for medical treatment of the cancerous tumors.

In certain embodiments, the conjugate is administered in a dose of up to 1 mCi for medical treatment of the cancerous tumors.

In certain embodiments, the conjugate is administered in a dose of up to 10 mCi for medical treatment of the cancerous tumors.

In certain embodiments, the conjugate is administered in a dose of up to 100 mCi for medical treatment of the cancerous tumors.

In certain embodiments, the conjugate is administered for more than a month.

In certain embodiments, the conjugate is administered for more than a year.

In certain embodiments, the conjugate is administered at a dosage of at least 0.05 µg/day.

The present invention provides in certain embodiments a use of the conjugate described above wherein:
a) the conjugate is administered simultaneously with the one or more anti-cancer agents; or
b) the conjugate and the one or more anti-cancer agents are administered sequentially; or
c) administration of the one or more anti-cancer agents begins about 1 to about 10 days before administration of the conjugate; or
d) administration of the conjugate thereof begins about 1 to about 10 days before administration of the one or more anti-cancer agents; or
e) administration of conjugate and administration of the one or more anti-cancer agents begins on the same day.

In certain embodiments, the ligand is a peptide.

In certain embodiments, the peptide is radiolabeled.

In certain embodiments, the SST2R-targeted ligand is a peptide that binds to the somatostatin receptor subtype 2.

In certain embodiments, the peptide is radiolabeled.

In certain embodiments, the agent that increases expression of SST2R is administered separately, sequentially or simultaneously with the SST2R-targeted ligand.

In certain embodiments, the agent that increases expression of SST2R is administered from about one day to about 6 months before the administration of the SST2R-targeted ligand.

In certain embodiments, the agent is administered orally or parenterally.

In certain embodiments, the agent is administered subcutaneously.

In certain embodiments, the SST2R-targeted ligand is administered orally or parenterally.

In certain embodiments, the administration of the agent begins about 1 to about 10 days before administration of the SST2R-targeted ligand.

In certain embodiments, the administration of the agent and administration of the SST2R-targeted ligand begin on the same day.

In certain embodiments, the method further comprises administering an anti-cancer composition.

BRIEF DESCRIPTION OF THE FIGURES

FIGS. 6A-6C. $^{203}$Pb SPECT/CT images in AR42J-tumor-bearing athymic nu/nu female mice. (A) AR42J-tumor-bearing mice were imaged at 3 h and 24 h post-injection after the administrations of 11.1 MBq $^{203}$Pb-DOTATOC and $^{203}$Pb-PSC-PEG$_2$-TOC. 30 nmol of unlabeled peptide was co-injected for the blocking imaging to confirm the tumor specificity. (B) Tumor-to-kidney ratio over time analyzed from the obtained images using the Inveon research workplace software. (C) The mice were euthanized at 30 h post-injection and biodistribution was obtained.

FIG. 5).

Figure 1A:
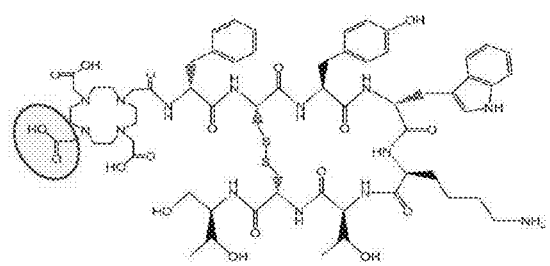
FIGS. 1A-1C. Structures of SST2R-targeted ligands DOTATOC (FIG. 1A), PSCTOC (FIG. 1B), and PSC-PEG$_2$/PEG4-TOC (FIG. 1C). The peptides were synthesized by the standard Fmoc-based solid phase peptide synthesis. They were based on tyr$^3$-octreotide (TOC), and DOTA or a new Pb-specific chelator (PSC) were conjugated. For the peptides with linkers, two different sizes of polyethylene glycol (PEG), PEG$_2$ and PEG$_4$, were inserted between PSC and the peptide backbone.
Figure 1B:
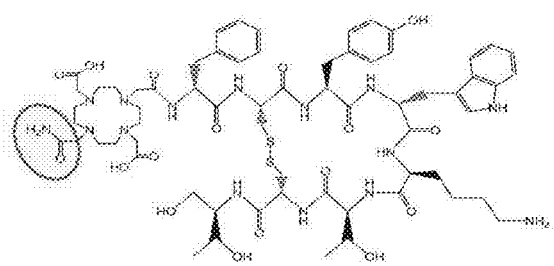
Figure 1C:
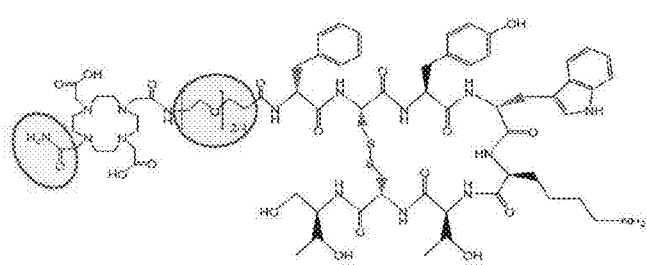
Figure 2A:
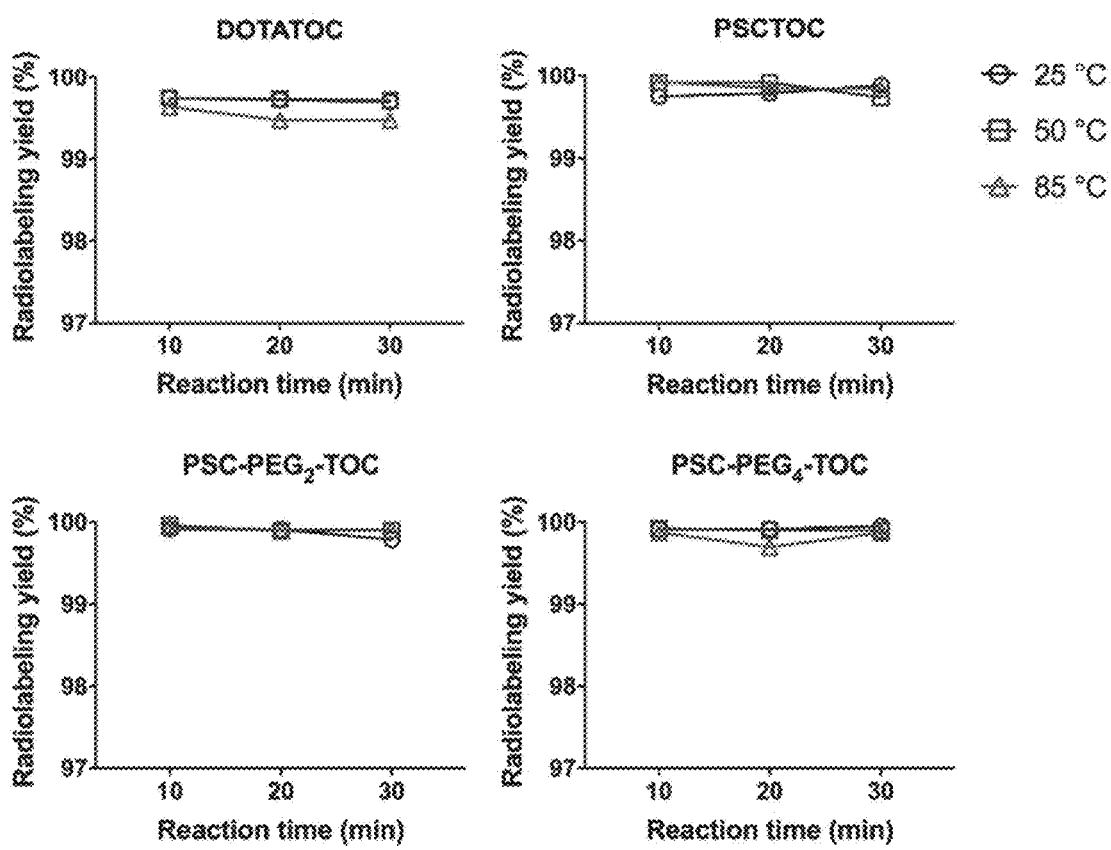
FIGS. 2A-2B. Excellent radiolabeling efficiency of SST2R-targeted ligands DOTATOC and the PSC-conjugated peptides with $^{203}$Pb (A) and $^{212}$Pb (B). 18.5 MBq of $^{203}$Pb or 14.1 MBq of $^{212}$Pb was reacted with 10 nmol peptides in 0.5 M sodium acetate (NaOAc) buffer (pH=5.4, 1 ml reaction volume). The reaction was conducted at various temperatures (25, 50, or 85° C.) and reaction time (10, 20, or 30 min) for the $^{203}$Pb labeling. DOTATOC and PSCTOC were selected for the $^{212}$Pb labeling, and the reaction was conducted at a fixed temperature (85° C.) with increasing time (up to 30 min).
Figure 2B:
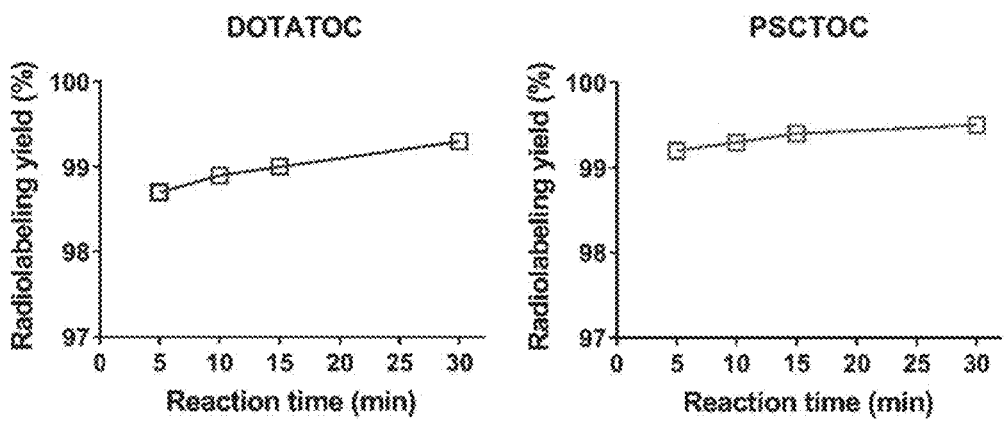
Figure 3:
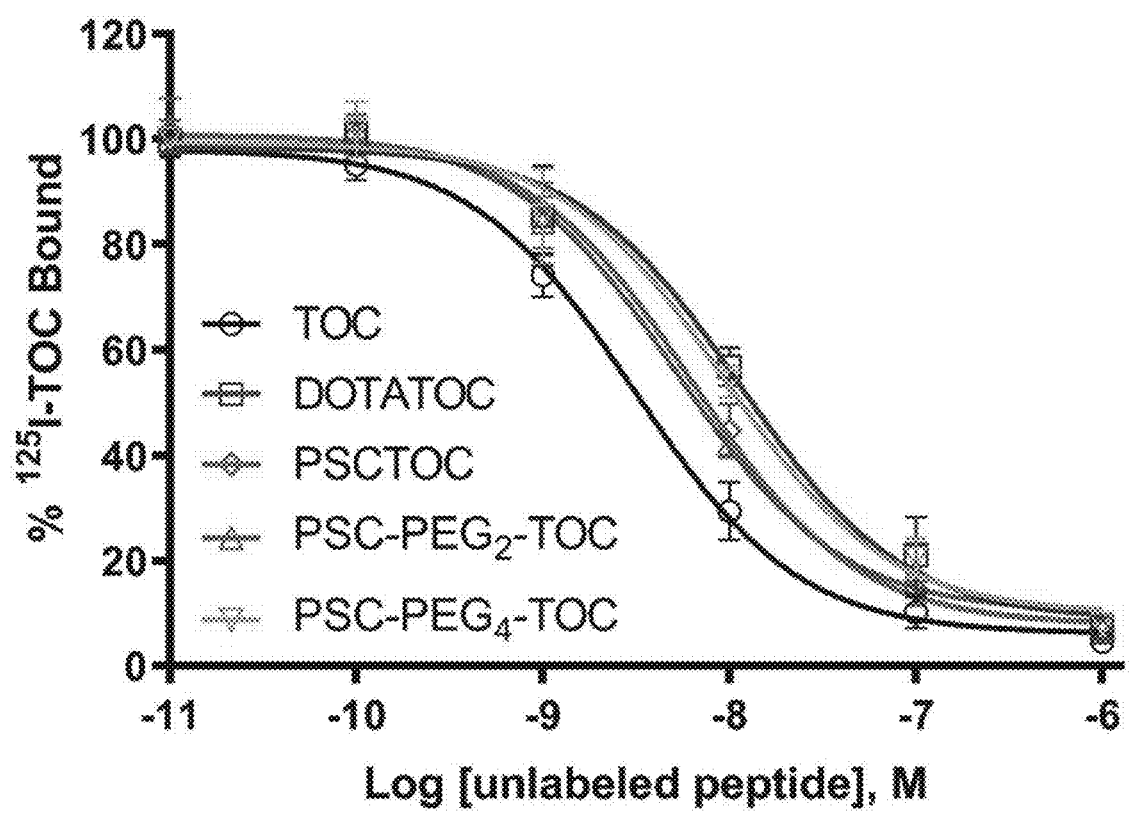
FIG. 3. Competitive inhibition of $^{125}$I-tyr$^3$-octreotide ($^{125}$I-TOC) binding to SSTR2-positive AR42J cells by TOC, DOTATOC, and the PSC-conjugated peptides. IC$_{50}$ values, TOC: 3.1±1.1 nM, DOTATOC: 11.3±1.3 nM, PSC-TOC: 6.2±1.1 nM, PSC-PEG$_2$-TOC: 5.3±1.2 nM, PSC-PEG$_4$-TOC: 9.4±1.3 nM (at least n=6 from at least three biological replicates for DOTATOC and PSCTOC; n=4-6 from two biological replicates for TOC, PSC-PEG$_2$-TOC, and PSC-PEG$_4$-TOC).
Figure 4:
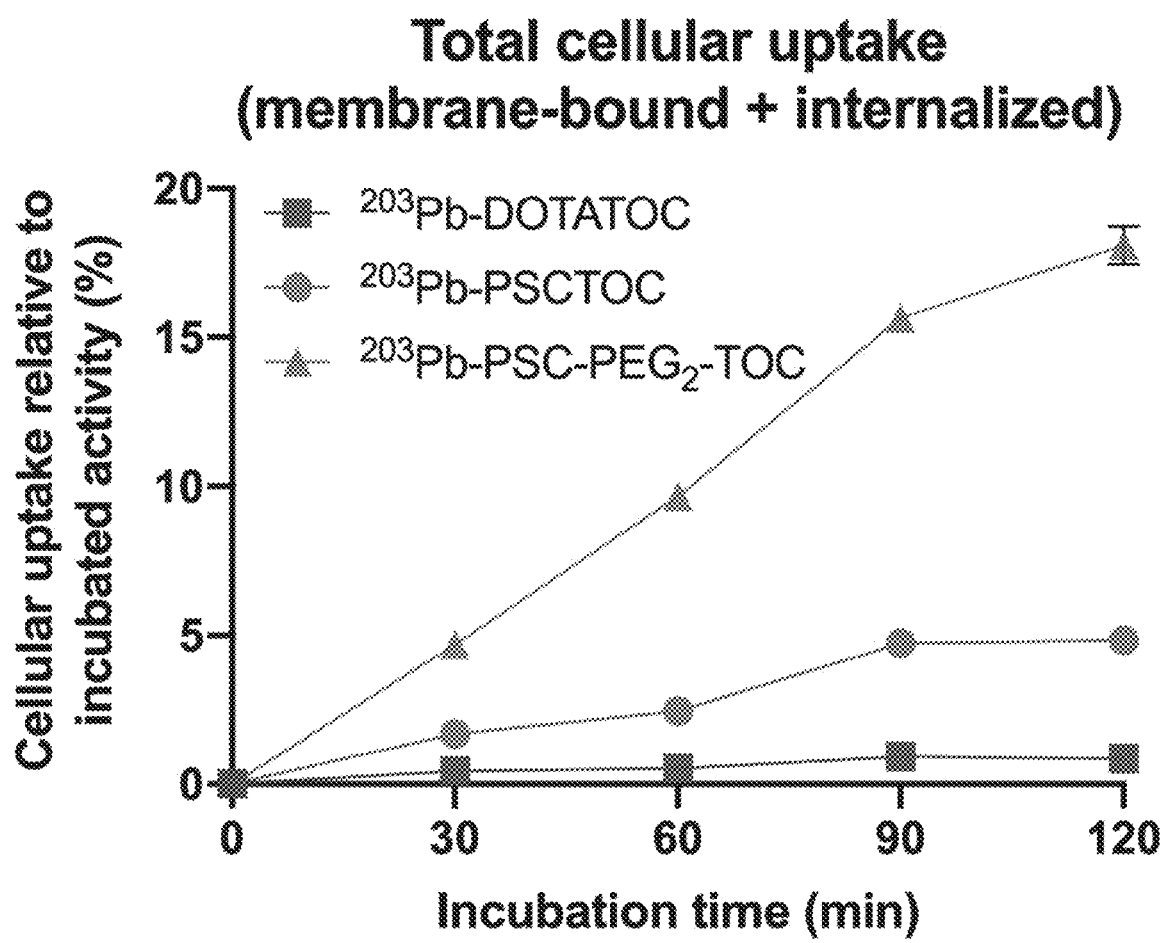
FIG. 4. Cellular uptake of $^{203}$Pb-labeled DOTATOC, PSCTOC, and PSC-PEG$_2$-TOC in AR42J cells. 200,000 CPM of HPLC-purified $^{203}$Pb-labeled peptides were incubated with AR42J SST2R expressing cells at 37° C. up to 120 min, and the cellular uptake of each radiotracer was measured. The data are shown as mean percentage of cellular uptake relative to incubated acitivties±SD (n=4).

The following example is intended to further illustrate the invention. It is not intended to limit the invention in any manner.

MATERIALS AND METHODS

Peptide Synthesis

DOTATOC, PSCTOC, PSC-PEG$_2$-TOC, and PSC-PEG$_4$-TOC were synthesized by the standard Fmoc-based solid phase peptide synthesis. The linear peptide, D-Phe-Cys-Tyr-D-Trp-Lys-Thr-Cys-Thr (ol) was synthesized on the resin at 100 µmol scale using an automated peptide synthesizer (AAPPTEC Apex 396) and the N-terminus of the linear peptide was deprotected by 25% piperidine (PIP) at the end of automated synthesis. The manual addition of the PEG linker ($PEG_2$ or $PEG_4$) was followed for $PSC-PEG_2$-TOC or $PSC-PEG_4$-TOC. The peptide-resin was suspended with N, N-dimethylformamide (DMF), and 5 equivalence (equiv.) of $Fmoc-NH-PEG_2/PEG_4$-propionic acid (purchased from AAPPTEC), 2-(7-aza-1H-benzotriazole-1-yl)-1,1,3,3-tetramethyluronium hexafluorophosphate (HATU), and 1-hydroxybenzotriazole (HOBt), and 10 equiv. of N, N-diisopropylethylamine (DIPEA) were added and reacted while being mixed at 37° C. for 2 h. The Fmoc on the N-terminus of the peptide-resin were then manually deprotected by 25% piperidine (in DMF) with mild mixing at 25° C. for 10 mins, and wash with DMF/Dichloromethane (DCM)/Methanol and repeated the process. The linear peptides with open N-terminus on the resin were then resuspended in DMF, and 5 equiv. of either DOTA-tris(tert-butyl ester) or PSC-bis (tert-butyl ester), HATU, and HOBt, and 10 equiv. of DIPEA were added and reacted at 37° C. while being mixed overnight. The success of each step of coupling/deprotection was verified by the Kaiser test and the process repeated until successful. The linear peptides were then cyclized by iodine oxidation. Iodine ($I_2$; 20 equiv.) was dissolved in 6 ml DMF and added to the peptide-resin and allowed reaction to proceed trityl deprotection from cysteine and concomitantly promote disulfide formation via oxidation for 3 h. The resin and protecting groups were then cleaved from the cyclized peptides by adding 3 mL cleavage cocktail (93% trifluoroacetic acid, 3% triisopropylsilane, 4% water) for 2 h at room temperature, followed by ether precipitation on ice for at least 4 h. The crude peptides were then purified by semi-preparative high performance liquid chromatography (HPLC) with a C-18 column (Vydac 10×250 mm, 10 µm; Grace, Deerfield, IL). The collected samples were concentrated by rotary evaporation, and lyophilized. The purified peptides were characterized by a mass spectrometer.

$^{203}Pb/^{212}Pb$ Radiolabeling Efficiency

DOTATOC and the PSC-conjugated peptides were radiolabeled with $^{203}Pb$ and $^{212}Pb$. 18.5 MBq of $^{203}Pb$ or 14.1 MBq of $^{212}Pb$ was reacted with 10 nmol peptides in 0.5 M Sodium Acetate (NaOAc) buffer (pH=5.4, 1 ml reaction volume). The reaction was conducted at various temperatures (25, 50, or 85° C.) and reaction time (10, 20, or 30 min) for the $^{203}Pb$ labeling. DOTATOC and PSCTOC were selected for the $^{212}Pb$ labeling, and the reaction was conducted at a fixed temperature (85° C.) with increasing time (up to 30 min). After the reaction, the resultant was spotted on pre-dried instant thin layer chromatography (iTLC) strips and developed by 10 mM diethylenetriaminepentaacetic acid (DTPA) in 0.1 M NaOAc buffer. The strips were then cut by half and the radio-activities of each portion (top, free $^{203}Pb/^{212}Pb$; bottom, $^{203}Pb/^{212}Pb$ labeled to the peptides) of the iTLC strips were measured by the isotope-specific gamma peaks ($^{203}Pb$, 279 keV; $^{212}Pb$, 239 keV) using a NaI detector.

$^{125}$I-TOC Competitive Binding Assay

TOC was labeled with iodine-125 ($^{125}$I) by conventional chloramine T method as described elsewhere (23). $1.0×10^5$ AR42J rat pancreatic acinar cells were plated into poly-D-lysine-coated 24-well plates. After 3 days, the cells were incubated with 30,000 CPM of $^{125}$I-TOC in binding medium (RPMI 1640 supplemented with 0.2% bovine serum albumin; 0.3 mM 1, 10-phenanthroline) with TOC, DOTATOC, PSCTOC, $PSC-PEG_2$-TOC, or $PSC-PEG_4$-TOC of increasing concentration ($10^{-11}$ to $10^{-6}$ M) for 2 hours at 37° C. The cells were then washed twice with ice-cold PBS and lysed with 0.5 N NaOH, and the radioactivity was measured via a gamma counter. The half maximal inhibitory concentration ($IC_{50}$) was determined using GraphPad Prism V8.0.

Internalization and Efflux of $^{203}Pb$-Labeled Peptides

37 MBq of $^{203}Pb$ was labeled with 10 nmol of DOTA-TOC, PSCTOC, and $PSC-PEG_2$-TOC, and the labeled peptides were separated from the unlabeled by high performance liquid chromatography (HPLC) based on differential retention times of the labeled and the unlabeled peptides by the previously developed separation method (15). The HPLC-separated radiopeptides were then purified by a C-18 cartridge. The AR42J cells that were plated with a density of $2.0×10^5$ cells 2 days before were incubated with 200,000 CPM of the HPLC-purified $^{203}Pb$-labeled peptides at 37° C. for up to 120 min. The cells were then washed twice with ice-cold PBS, and the membrane-bound radioactivity was washed off by 50 mM acidic (pH=4) sodium acetate buffer and collected. The remaining cells were lysed by adding 0.5N NaOH for 5 min. The radioactivity of each portion (membrane-bound and internalized) was counted by a 310 Cobra II gamma counter (PerkinElmer, Freemont, CA). For the efflux assay, the cells were incubated with 200,000 CPM of the HPLC-purified $^{203}Pb$-labeled peptides at 37° C. for 120 min. The cells were then washed twice with ice-cold PBS and replenished with the binding medium. After 60 min and 120 min, the radioactivities of the effluxed (into the medium), the membrane-bound and the internalized (harvested by the same way as in the internalization assay) were counted.

Biodistribution of $^{203}Pb$-Labeled Peptides 37 kBq of $^{203}Pb$-labeled DOTATOC, PSCTOC, and $PSC-PEG_2$-TOC (specific activity: 22.2 MBq/nmol) were injected into female AR42J tumor-bearing athymic nu/nu mice via tail vein. The mice were euthanized at 1, 3, and 24 h post-injection by cervical dislocation under isoflurane anesthesia. Tumor and organs/tissues of interest were harvested and the weights of the collected organs/tissues were measured. The radioactivities of the samples were measured by the PerkinElmer 310 Cobra II gamma counter (PerkinElmer, Freemont, CA).

Tumor and Kidney Dosimetry

The Particle and Heavy Ion Transport code System (PHITS) was used for dosimetry analysis. For the kidney dosimetry, DigiMouse voxel phantom model was used, and the voxel size of the model was adjusted so that the volume of the kidneys became identical to the average volume of the kidneys of female athymic nude mice (288.7+−41.4 mg; 28 mice) from the biodistribution study (AR42J bearing; 8-10 weeks). The elemental composition of the kidney and the mass density was assumed to be identical as the human reference adults' values obtained from the International Commission on Radiation Units and measurements (ICRU) report 46. For tumor dosimetry, a spherical volume was constructed based on the average tumor mass (156.9+−0.096 mg) of the 28 mice. The elemental composition (adenoidcystic carcinoma) and mass density (1.04 g/cm$^3$) of the tumor was adapted from Maughan et al. 1997 Med Phys 24 (8): 1241-4 and R M Thomson et al. 2013 Phys. Med. Biol. 58:1123-50. At least 1 million particles were transported for the Monte Carlo simulations to reduce the statistical uncertainties less than 1%.

Serial SPECT/CT Imaging of $^{203}Pb$-DOTATOC Vs. $^{203}Pb$-$PSC-PEG_2$-TOC 1.85 GBq (50 mCi; 61.7 MBq/nmol) of $^{203}Pb$ was labeled with DOTATOC and $PSC-PEG_2$-TOC. 11.1 MBq of each $^{203}Pb$ labeled peptide was injected into AR42J bearing mice via tail vein, and the mice was imaged at 3 h and 24 h post-injection. Separately, the same activity of $^{203}$Pb-PSC-PEG$_2$-TOC was co-injected with 30 nmol of unlabeled PSC-PEG$_2$-TOC for the blocking study to confirm the tumor specificity of the radiotracer. The images were reconstructed and analyzed with the same parameter setting using the Inveon research workplace software. Standardized uptake values corrected by body weight (SUVbw) were analyzed, and the biodistributions of the mice were obtained at 30 h post-administration.

Stability of $^{203}$Pb-PSC-PEG$_2$-TOC in Water and Human Serum

As the identified lead compound, PSC-PEG$_2$-TOC was further evaluated in various aspects. PSC-PEG$_2$-TOC was radiolabeled with 50 MBq (1.34 mCi) of $^{203}$Pb and purified by C-18. 9 MBq (0.24 mCi) of purified radiopeptide was added into 3 ml water or human serum and incubated at 37° C. for up to 24 h. After incubation, the serum samples with $^{203}$Pb-PSC-PEG$_2$-TOC were transferred to Amicon Ultra Centrifugal Filter (3K; Millipore) and centrifuged by a Beckman Coulter Avanti J-25I centrifuge. The penetrates by centrifugation (serum sample) or the samples in water were analyzed by a radio-HPLC system (Agilent 1200 Series connected with an IN/US β-RAM Model 4 radio-detector) to monitor the degree of peptide degradation.

Clinically-Relevant High Specific Activity $^{203}$Pb Radiolabeling of PSC-PEG$_2$-TOC PSC-PEG$_2$-TOC were radiolabeled with $^{203}$Pb at high specific activities of either 90 MBq/nmol or 120 MBq/nmol. DOTATOC was also labeled in 90 MBq/nmol for reference. The reactions were conducted in 0.5 M Sodium Acetate (NaOAc) buffer (pH=5.4, 1-2 ml reaction volume) at 85° C. for 30 min. 2 μl of reaction product containing $^{203}$Pb-labeled peptide was spotted on an instant thin layer chromatography (iTLC) strip. The sample strip was developed in the mobile phase (0.2 M sodium acetate with 20 mM EDTA) and then imaged with a phosphor imager (Typhoon FLA7000). The strip was cut by half and the radioactivity of each side of strip was measured by the NaI detector by $^{203}$Pb gamma peak (279 keV) to determine the radiolabeling efficiency.

Figures 5A, 5B:
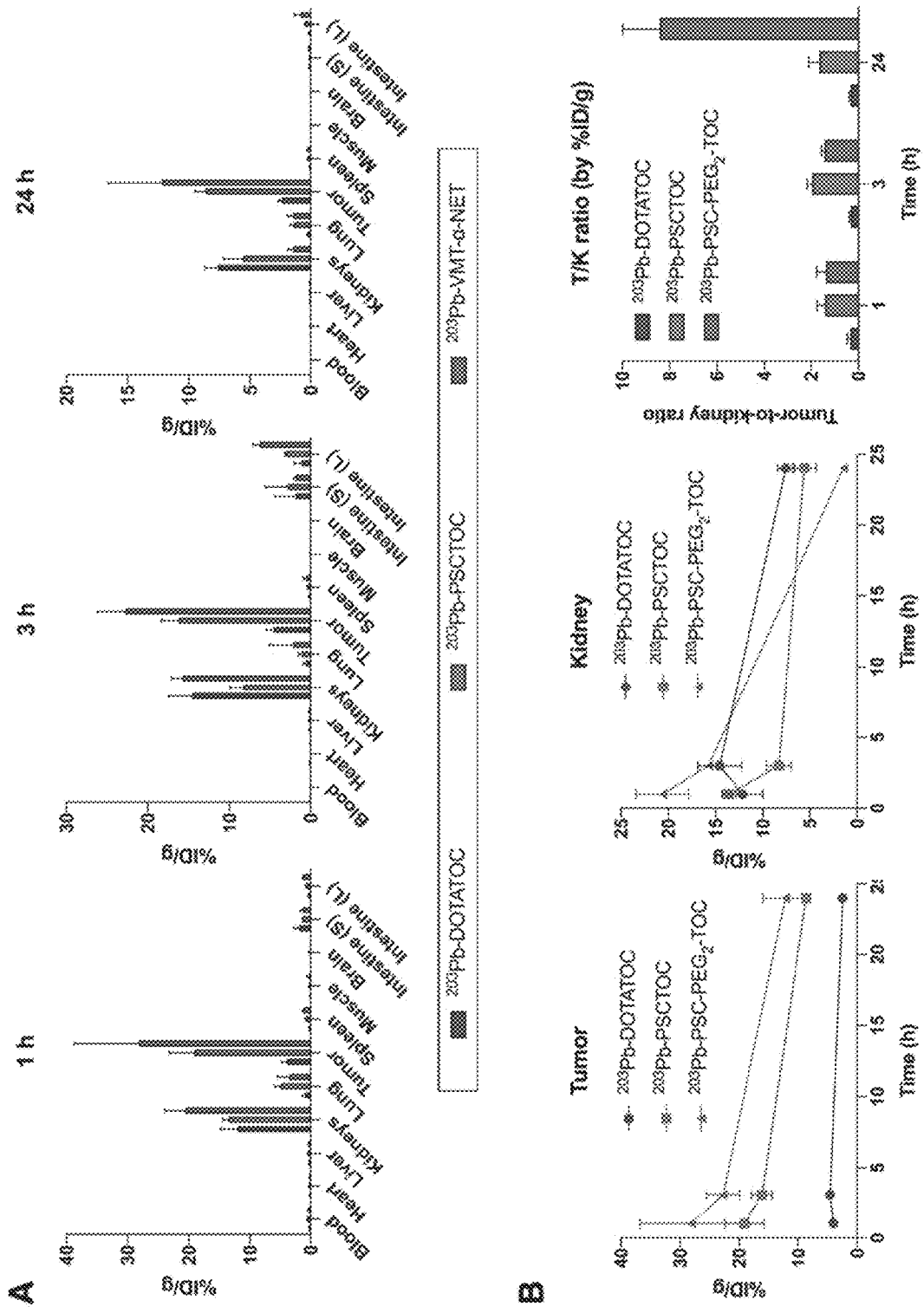
FIGS. 5A-5B. Biodistribution of $^{203}$Pb-labeled SST2R-targeted DOTATOC, PSCTOC, and PSC-PEG$_2$-TOC in AR42J tumor bearing athymic nude mice. Biodistribution was observed at 1, 3, and 24 h post-injection after the i.v. injections of 37 kBq $^{203}$Pb-labeled peptides (A), and percent injection dose per gram of tissue (% ID/g) over time for tumor and kidneys as well as tumor-to-kidney ratio were shown (B). The data is shown in mean percent injected dose per gram of tissue (% ID/g) or relative mean tumor-to-kidney ratio±S.D. (n=3).
Figure 7:
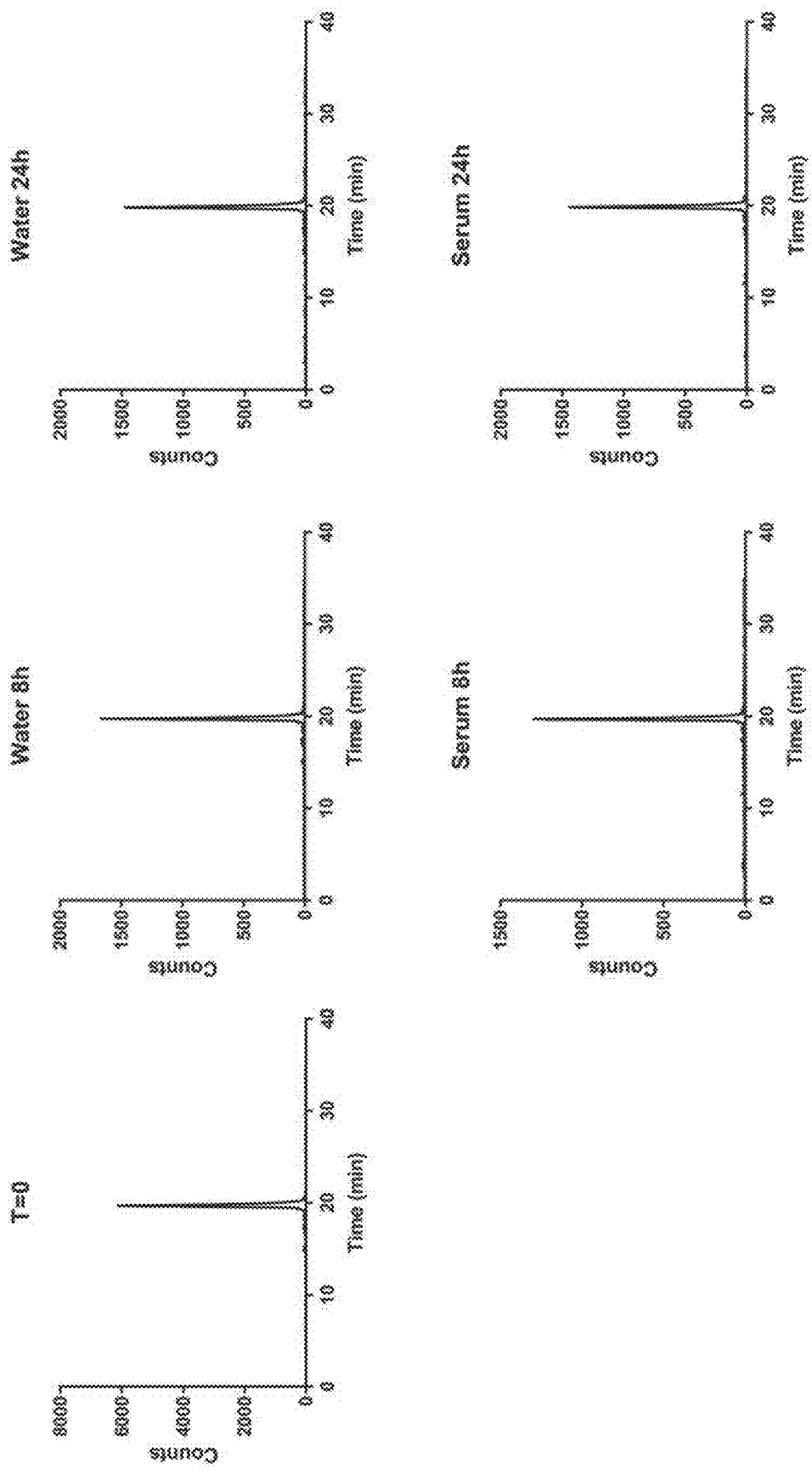
FIG. 7. Stability of PSC-PEG$_2$-TOC in water and human serum. PSC-PEG$_2$-TOC was radiolabeled with 50 MBq (1.34 mCi) of $^{203}$Pb, and 9 MBq (0.24 mCi) of purified radiopeptide was added into 3 ml water or human serum and incubated at 37° C. for up to 24 h. The peptide degradation was monitored by a radio-HPLC system (Agilent 1200 Series connected with an IN/US β-RAM Model 4 radio-detector) after 8 h and 24 h.
Figure 8:
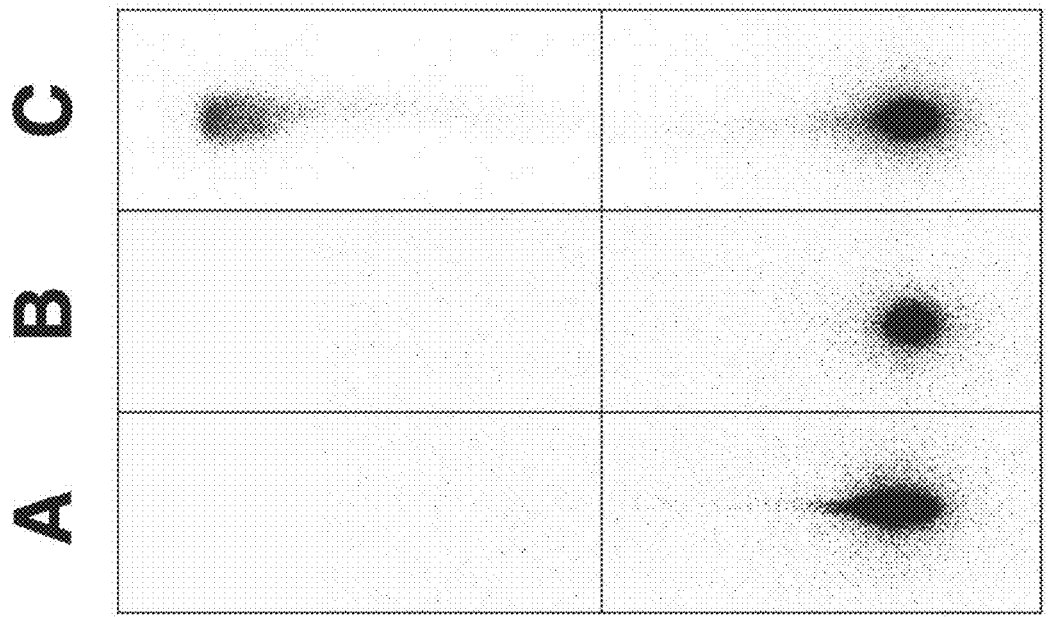
FIG. 8. Clinically-relevant high specific activity $^{203}$Pb radiolabeling of PSC-PEG$_2$-TOC. The radiolabeling was conducted with high activities of $^{203}$Pb at either 90 MBq/nmol DOTATOC for reference (A), 90 MBq/nmol PSC-PEG$_2$-TOC (B), or 120 MBq/nmol PSC-PEG$_2$-TOC (C) in 0.5 M Sodium Acetate (NaOAc) buffer (pH=5.4, 1-2 ml reaction volume) at 85° C. for 30 min.
Figure 8:
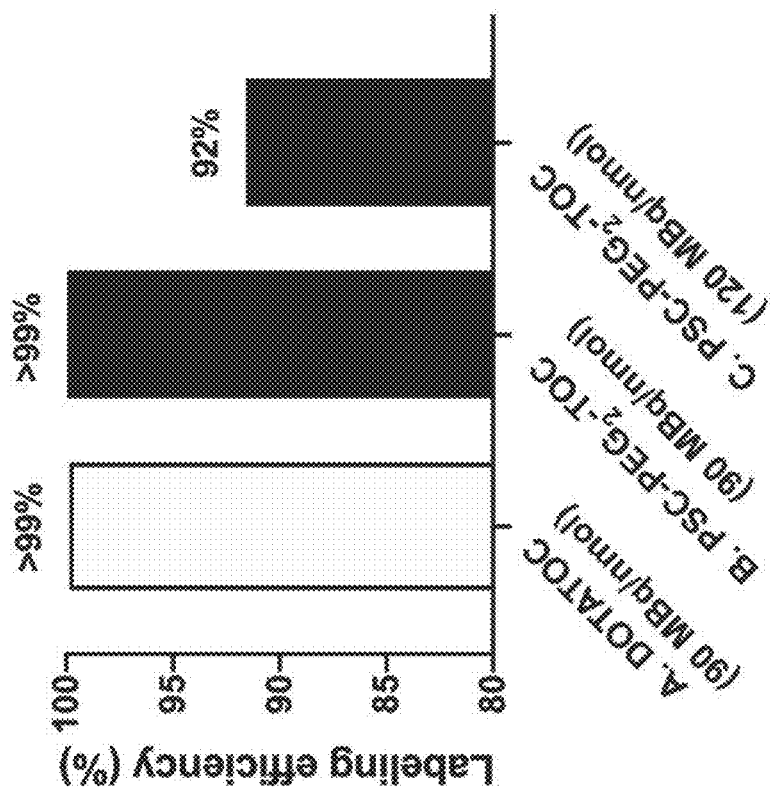
Figure 9:
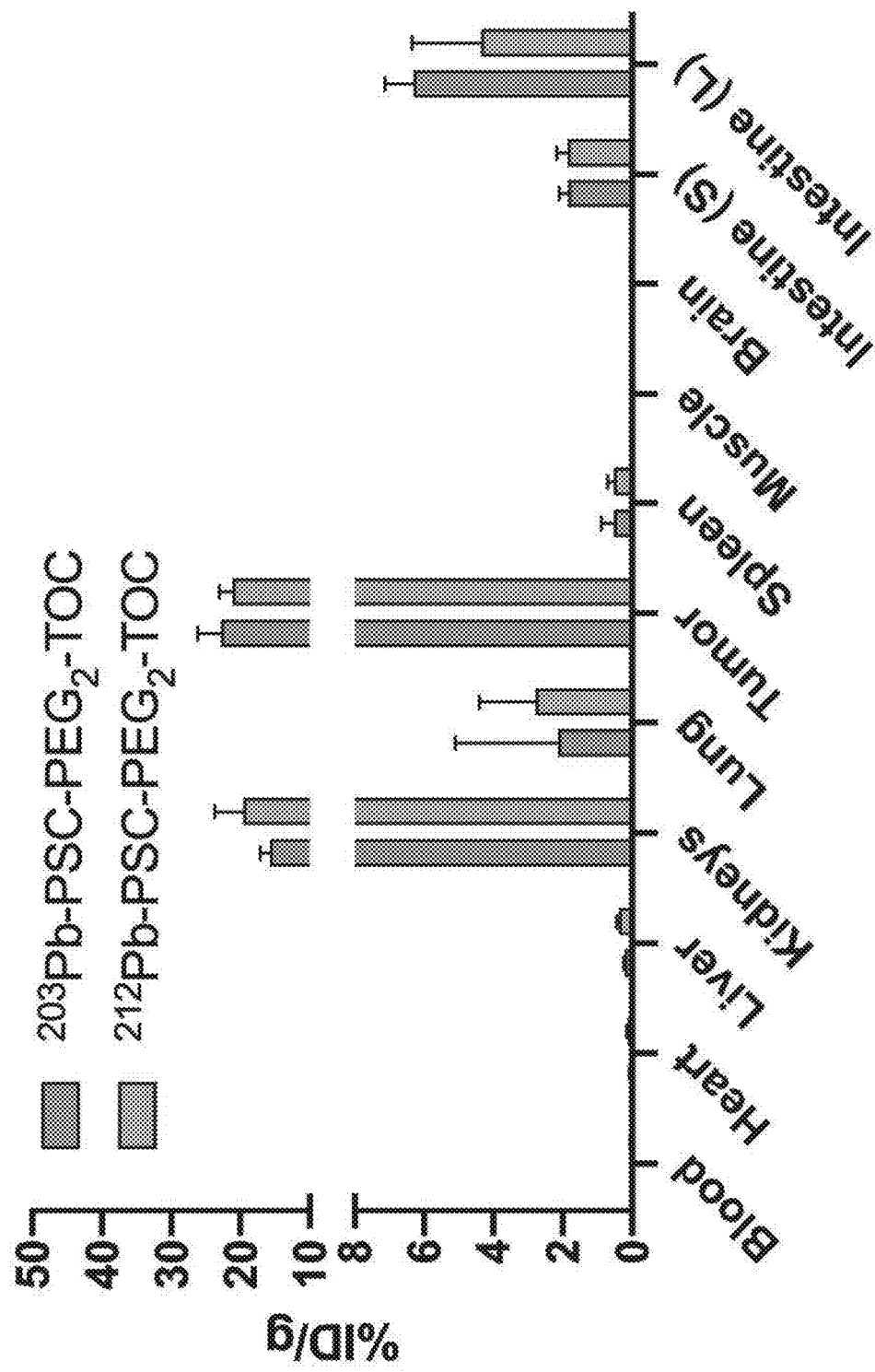
FIG. 9. Biodistribution of $^{203}$Pb/$^{212}$Pb-labeled PSC-PEG$_2$-TOC in AR42J tumor bearing athymic nude mice at 3 h post-injection. 74 kBq of $^{212}$Pb-PSC-PEG$_2$-TOC (specific activities, 3.7 MBq/nmol) was injected via tail vein and the biodistribution was obtained at 3 h post-injection (n=4). This data was directly compared to the biodistribution of $^{203}$Pb-PSC-PEG$_2$-TOC obtained previously (specific activity, 22.2 MBq/nmol.
Figure 10A:
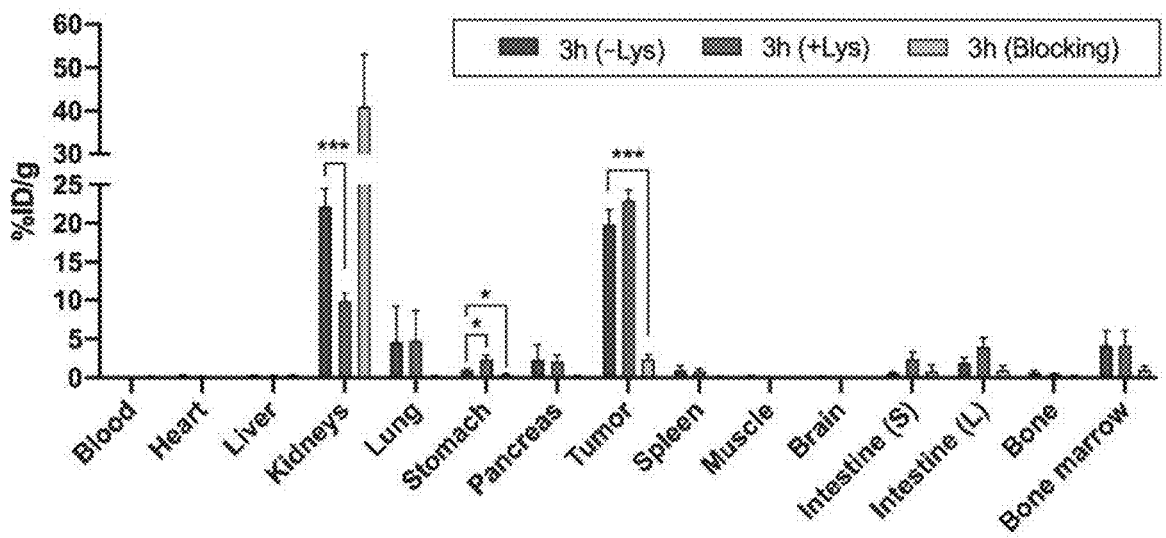
FIGS. 10A-10B. Reduced renal accumulation of $^{203}$Pb-PSC-PEG$_2$-TOC by DL-lysine co-injection, and specific tumor binding of the radiopeptide in AR42J bearing nude mice informed by tumor blocking with co-injection of excess unlabeled peptide. (A) Biodistribution of $^{203}$Pb-PSC-PEG$_2$-TOC at 3 h post-injection in AR42J-tumor-bearing nude mice with lysine co-injection (400 mg/kg), without lysine co-injection, or with unlabeled peptide co-injection (for tumor blocking; 10 nmol PSC-PEG$_2$-TOC). (B) Complete biodistribution of $^{203}$Pb-PSC-PEG$_2$-TOC with DL-lysine co-injection (400 mg/kg) at 1, 3, 6, and 24 h post-injection. Results are in percent injected dose per gram of tissue (% ID/g)±S.D. (n=3).
Figure 10B:
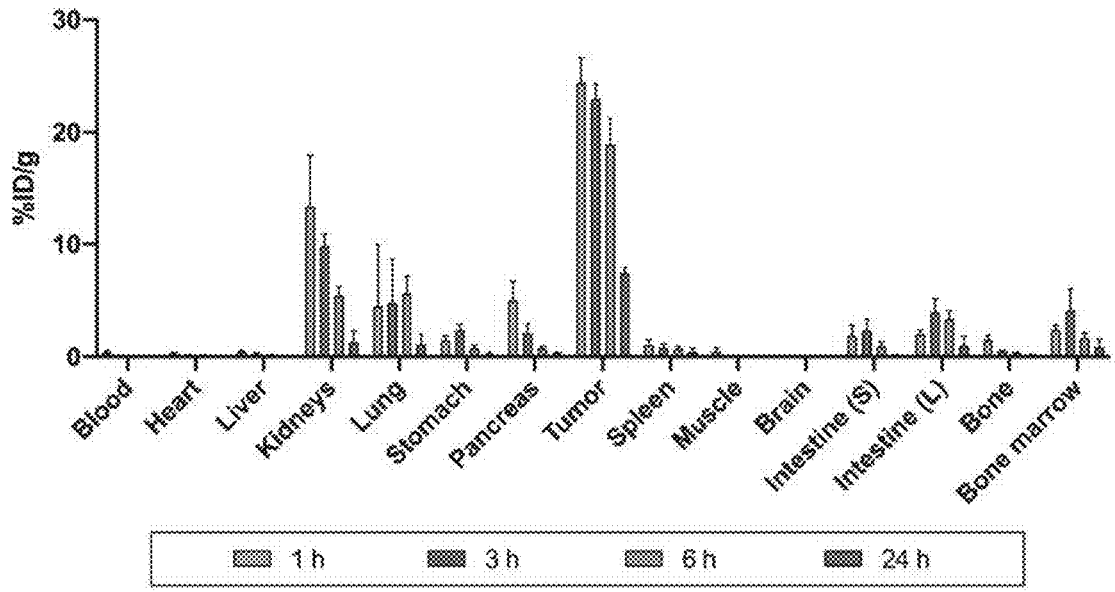
Figures 11A, 11B, 11C:
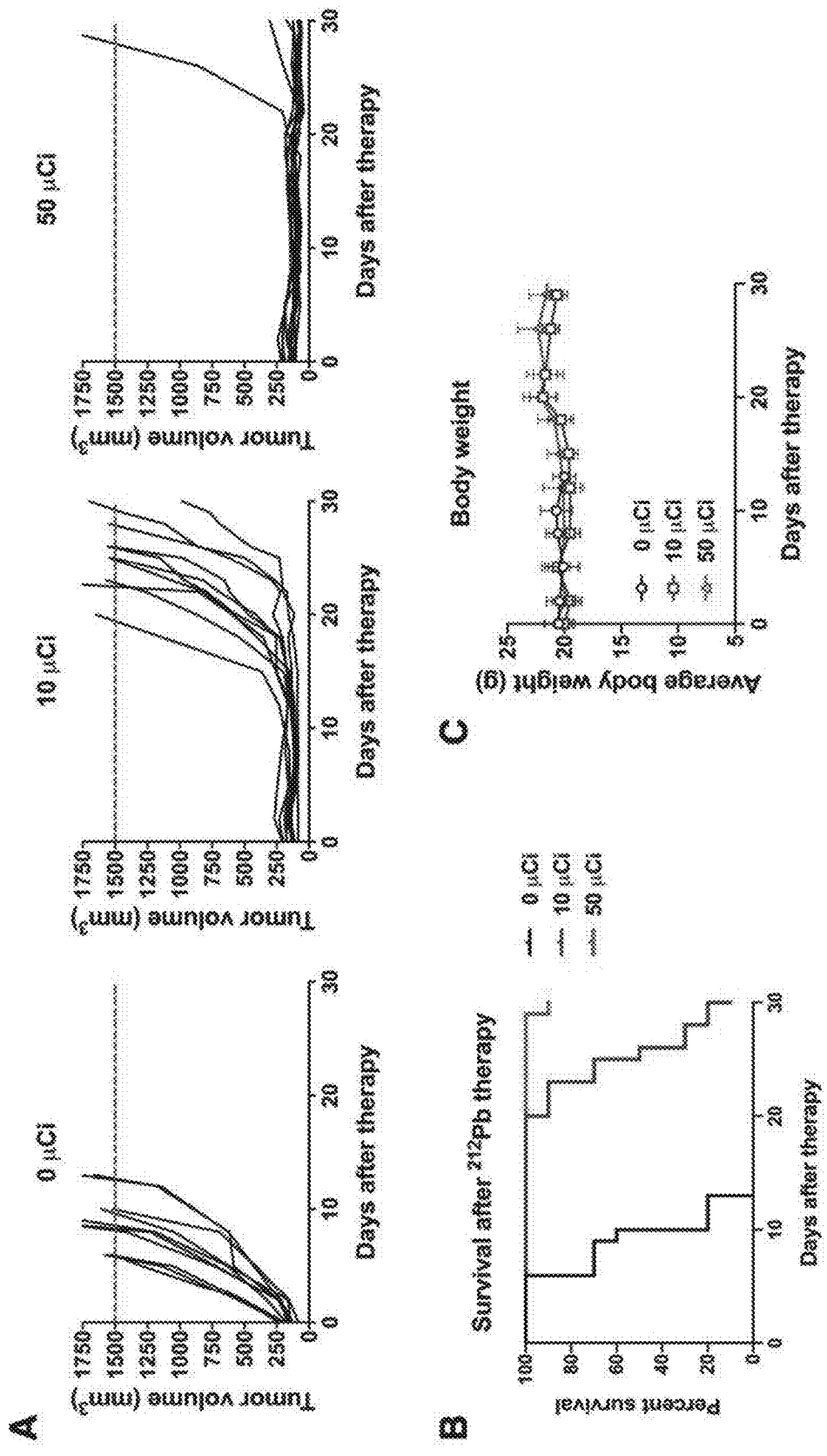
FIGS. 11A-11C. Therapeutic outcomes of initial $^{212}$Pb-PSC-PEG$_2$-TOC therapy studies in mice bearing AR42J-SST2R-expressing tumors at 30 days post-therapy. $^{212}$Pb-PSC-PEG$_2$-TOC therapy was initiated when the average tumor size became around 150 mm$^3$. 0.37 MBq (10 μCi) and 1.85 MBq (50 μCi) of $^{212}$Pb-PSC-PEG$_2$-TOC were injected via tail vein with DL-lysine (400 mg/kg) co-injection to block the kidney uptake of the radiotherapeutic.
Figures 12A, 12B, 12C, 12D, 12E, 12F:
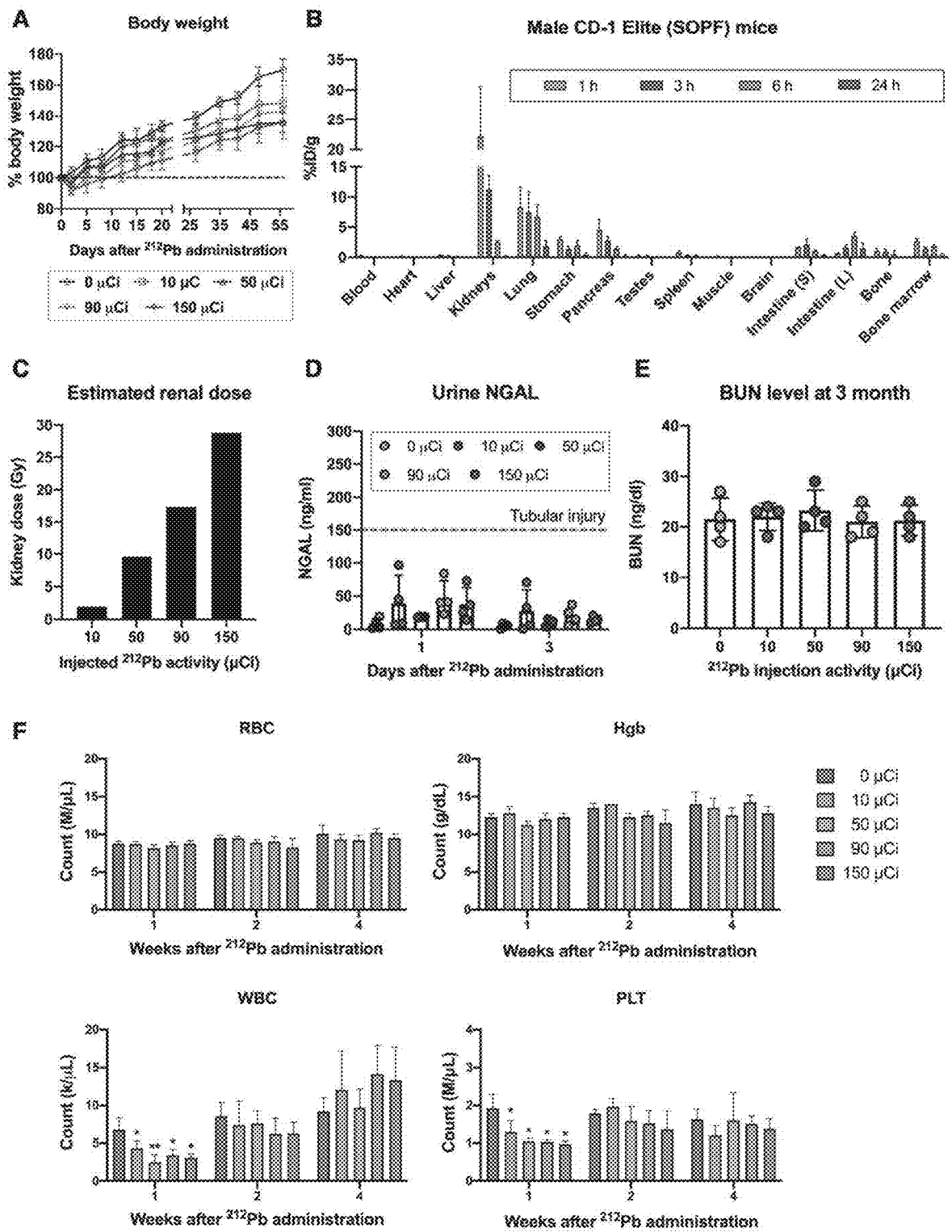
FIG. 12A-12F. Dosimetry and toxicities of escalated doses (up to 150 μCi) of $^{212}$Pb—PSC-PEG$_2$-TOC in CD-1 Elite (SOPF) male mice. (A) Body weight change after the injection of $^{212}$Pb-PSC-PEG$_2$-TOC. After an initial decrease in body weight in first days, the body weight of the treated mice increased gradually in which the increase of the body weight is dose-dependent. (B) $^{212}$Pb-PSC-PEG$_2$-TOC biodistribution in CD-1 Elite (SOPF) male mice. $^{212}$Pb is used for the study to include the impact of potential demetallation of $^{212}$Pb and redistribution in bone marrow. (C) Estimated renal dose arising from the escalating doses of $^{212}$Pb-PSC-PEG$_2$-TOC based on the biodistribution in CD-1 Elite (SOPF) male mice. Organ level internal dose assessment (OLINDA) V2.1 was used for dose estimation in mice using 30 g mouse voxel phantom model. (D-E) The levels of renal toxicity markers arising from the escalating doses of $^{212}$Pb-PSC-PEG$_2$-TOC assessed by urine neutrophil gelatinase-associated lipocalin (uNGAL; D) at day 1 and day 3 post-administration and blood urea nitrogen (BUN; E) at 3 months post-administration. (F) A reversible hematologic toxicity indicated by complete blood count (CBC) at week 1, 2, and 4 post-administration.

Biodistribution of $^{212}$Pb-PSC-PEG$_2$-TOC in AR42J Bearing Nude Mice 74 kBq of $^{212}$Pb-PSC-PEG$_2$-TOC (specific activity, 3.7 MBq/nmol) was injected into AR42J bearing athymic nude mice via tail vein and the biodistribution was obtained at 3 h post-injection (n=4). This data was directly compared to the biodistribution of $^{203}$Pb-PSC-PEG$_2$-TOC obtained previously (specific activity, 22.2 MBq/nmol; FIG. 5). The data determined the adequacy of $^{203}$Pb-PSC-PEG$_2$-TOC as the imaging and dosimetry surrogate for $^{212}$Pb-PSC-PEG$_2$-TOC.

Biodistribution of $^{203}$Pb-PSC-PEG$_2$-TOC in AR42J Bearing Nude Mice with Lysine Co-Infusion 37 kBq of $^{203}$Pb-PSC-PEG$_2$-TOC (specific activity: 22.2 MBq/nmol) was injected into AR42J tumor-bearing nude mice via tail vein with and without co-injection of DL-lysine (400 mg/kg; 8 mg/animal) to observe if lysine co-injection could reduce the non-specific renal uptake of the radiotracer. Also, a separate group was added for tumor blocking to verify the specificity of tumor targeting by co-injecting 10 nmol of unlabeled peptide (without lysine) with 37 kBq of $^{203}$Pb-PSC-PEG$_2$-TOC. These mice were then euthanized at 3 h post-injection and biodistribution was assessed (n=3 for each group). In a separate study, comprehensive biodistribution was obtained at 1, 3, 6, and 24 h post-injection with co-injection of DL-lysine to acquire complete pharmacokinetic data for further dosimetry studies.

212 Pb-PSC-PEG$_2$-TOC Therapy 5.0×10$^6$ AR42J rat pancreatic acinar cells were implanted on the left shoulder of female athymic nu/nu mice. After 10 days, when the average tumor size became around 150 mm$^3$, 274 MBq (7.4 mCi) $^{212}$Pb were reacted with 30 nmol PSC-PEG$_2$-TOC (9.1 MBq/nmol) in the presence of ascorbic acid (1 mg/ml) for 20 min at 85° C. After reaction, the radio-peptide were purified by C-18 and resuspended with saline containing ascorbic acid (1 mg/ml). 0.37 MBq (10 μCi) and 1.85 MBq (50 μCi) of $^{212}$Pb-PSC-PEG$_2$-TOC were injected via tail vein. DL-lysine (400 mg/kg) was co-injected to block the kidney uptake of the radiotherapeutic.

$^{212}$Pb-PSC-PEG$_2$-TOC Toxicity Studies

Escalating doses (0, 0.37, 1.85, 3.33, and 5.55 MBq or 0, 10, 50, 90, and 150 μCi) of $^{212}$Pb-PSC-PEG$_2$-TOC were administered to tumor-free CD-1 Elite (SOPF) male mice (n=4 for each group). Body weight was measured 2 times a week by 3 weeks post-injection and 1 time a week afterwards. Urine samples were collected (via metabolic case) at day 1 and day 3 post-administration to evaluate acute tubular toxicities in kidneys. The urine samples were centrifuged, and the levels of urine neutrophil gelatinase-associated lipocalin (uNGAL) were measured using a mouse NGAL ELISA kit (Kit 042; BIOPORTO Diagnostics) according to the manufacturer's manual. At 3 months post-injection, the serum samples were collected by tail vein nicking, sent to IDEXX Laboratories, inc., and analyzed for comprehensive blood chemistry including blood urea nitrogen (BUN). Further follow-up will be made at 6-7 months for the comprehensive blood chemistry test and kidney histopathology analysis. The hematological toxicity was assessed by complete blood counts (CBC) using an automated veterinary hematology analyzer (ADVIA 120, Siemens Healthineers) at week 1, 2, and 4 post-administration. In addition, $^{212}$Pb-PSC-PEG$_2$-TOC biodistribution study was conducted at 1, 3, 6, and 24 h (including bone marrow), to support dosimetry analyses that can correlate with toxicity profile in critical organs/tissues including kidneys and bone marrow. Dose estimation was performed in Organ Level Internal Dose Assessment (OLINDA, V2.1) software using 30 g mouse voxel phantom model.

REFERENCES

1. Dasari A, Shen C, Halperin D, et al. Trends in the Incidence, Prevalence, and Survival Outcomes in Patients With Neuroendocrine Tumors in the United States. *JAMA Oncol.* 2017; 3:1335-1342.
2. Oronsky B, Ma P C, Morgensztern D, Carter C A. Nothing But NET: A Review of Neuroendocrine Tumors and Carcinomas. *Neoplasia.* 2017; 19:991-1002.
3. Kaemmerer D, Trager T, Hoffmeister M, et al. Inverse expression of somatostatin and CXCR4 chemokine receptors in gastroenteropancreatic neuroendocrine neoplasms of different malignancy. *Oncotarget.* 2015; 6:27566-27579.
4. Imhof A, Brunner P, Marincek N, et al. Response, survival, and long-term toxicity after therapy with the radiolabeled somatostatin analogue [$^{90}$Y-DOTA]-TOC in metastasized neuroendocrine cancers. *J Clin Oncol.* 2011; 29:2416-2423.
5. Marincek N, Jorg A C, Brunner P, et al. Somatostatin-based radiotherapy with [$^{90}$Y-DOTA]-TOC in neuroendocrine tumors: long-term outcome of a phase I dose escalation study. *J Transl Med.* 2013; 11:17.

6. Strosberg J, El-Haddad G, Wolin E, et al. Phase 3 Trial of [177]Lu-Dotatate for Midgut Neuroendocrine Tumors. *New England Journal of Medicine.* 2017; 376:125-135.
7. Kwekkeboom D J, de Herder W W, Kam B L, et al. Treatment with the radiolabeled somatostatin analog [177 Lu-DOTA 0, Tyr3] octreotate: toxicity, efficacy, and survival. *J Clin Oncol.* 2008; 26:2124-2130.
8. Brabander T, van der Zwan W A, Teunissen J J M, et al. Long-Term Efficacy, Survival, and Safety of [(177) Lu-DOTA (0), Tyr (3)] octreotate in Patients with Gastroenteropancreatic and Bronchial Neuroendocrine Tumors. *Clin Cancer Res.* 2017; 23:4617-4624.
9. FDA Approves Lutathera for GEP NET Therapy. *J Nucl Med.* 2018; 59: 9N.
10. Lee D, Li M, Bednarz B, Schultz M K. Modeling Cell and Tumor-Metastasis Dosimetry with the Particle and Heavy Ion Transport Code System (PHITS) Software for Targeted Alpha-Particle Radionuclide Therapy. *Radiat Res.* 2018; 190:236-247.
11. Sgouros G, Roeske J C, McDevitt M R, et al. MIRD Pamphlet No. 22 (abridged): radiobiology and dosimetry of alpha-particle emitters for targeted radionuclide therapy. *J Nucl Med.* 2010; 51:311-328.
12. Kratochwil C, Bruchertseifer F, Giesel F L, et al. 225Ac-PSMA-617 for PSMA-Targeted alpha-Radiation Therapy of Metastatic Castration-Resistant Prostate Cancer. *J Nucl Med.* 2016; 57:1941-1944.
13. Kratochwil C, Giesel F L, Bruchertseifer F, et al. 213Bi-DOTATOC receptor-targeted alpha-radionuclide therapy induces remission in neuroendocrine tumours refractory to beta radiation: a first-in-human experience. *Eur J Nucl Med Mol Imaging.* 2014; 41:2106-2119.
14. Dos Santos J C, Schafer M, Bauder-Wust U, et al. Development and dosimetry of (203) Pb/(212) Pb-labelled PSMA ligands: bringing "the lead" into PSMA-targeted alpha therapy? *Eur J Nucl Med Mol Imaging.* 2019; 46:1081-1091.
15. Li M, Zhang X, Quinn T P, et al. Automated cassette-based production of high specific activity [(203/212) Pb] peptide-based theranostic radiopharmaceuticals for image-guided radionuclide therapy for cancer. *Appl Radiat Isot.* 2017; 127:52-60.
16. Chen J, Cheng Z, Owen N K, et al. Evaluation of an (111) In-DOTA-rhenium cyclized alpha-MSH analog: a novel cyclic-peptide analog with improved tumor-targeting properties. *J Nucl Med.* 2001; 42:1847-1855.
17. Martin M E, Sue O'Dorisio M, Leverich W M, Kloepping K C, Walsh S A, Schultz M K. "Click"-cyclized (68) Ga-labeled peptides for molecular imaging and therapy: synthesis and preliminary in vitro and in vivo evaluation in a melanoma model system. *Recent Results Cancer Res.* 2013; 194:149-175.
18. Guo H, Miao Y. Introduction of an 8-aminooctanoic acid linker enhances uptake of 99mTc-labeled lactam bridge-cyclized alpha-MSH peptide in melanoma. *J Nucl Med.* 2014; 55:2057-2063.
19. Schweinsberg C, Maes V, Brans L, et al. Novel glycated [99mTc(CO)3]-labeled bombesin analogues for improved targeting of gastrin-releasing peptide receptor-positive tumors. *Bioconjug Chem.* 2008; 19:2432-2439.
20. Chappell L L, Dadachova E, Milenic D E, Garmestani K, Wu C, Brechbiel M W. Synthesis, characterization, and evaluation of a novel bifunctional chelating agent for the lead isotopes [203]Pb and [212]Pb. *Nucl Med Biol.* 2000; 27:93-100.
21. Gourni E, Mansi R, Jamous M, et al. N-terminal modifications improve the receptor affinity and pharmacokinetics of radiolabeled peptidic gastrin-releasing peptide receptor antagonists: examples of 68Ga- and 64Cu-labeled peptides for PET imaging. *J Nucl Med.* 2014; 55:1719-1725.
22. Lin M, Welch M J, Lapi S E. Effects of chelator modifications on (68) Ga-labeled [Tyr (3)]octreotide conjugates. *Mol Imaging Biol.* 2013; 15:606-613.
23. de Blois E, Chan H S, Breeman W A. Iodination and stability of somatostatin analogues: comparison of iodination techniques. A practical overview. *Curr Top Med Chem.* 2012; 12:2668-2676.

It should be appreciated that minor dosage and formulation modifications of the composition and the ranges expressed herein may be made and still come within the scope and spirit of the present invention.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

The foregoing description has been presented for the purposes of illustration and description. It is not intended to be an exhaustive list or limit the invention to the precise forms disclosed. It is contemplated that other alternative processes and methods obvious to those skilled in the art are considered included in the invention. The description is merely examples of embodiments. It is understood that any other modifications, substitutions, and/or additions may be made, which are within the intended spirit and scope of the disclosure. From the foregoing, it can be seen that the exemplary aspects of the disclosure accomplishes at least all of the intended objectives.

What is claimed:

1. A compound having the following structure:

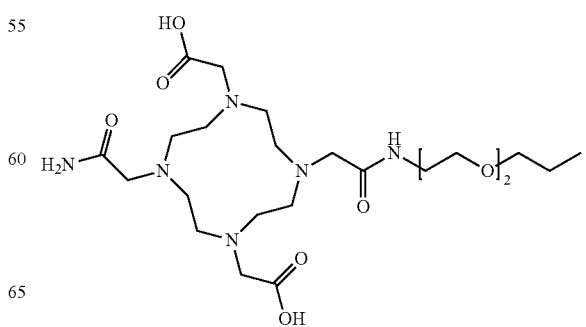

-continued
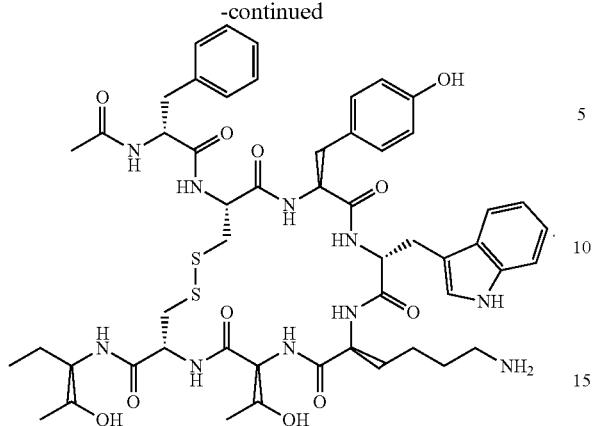
2. The compound of claim 1, wherein the compound is labeled with $^{203}$Pb or $^{212}$Pb.
3. The compound of claim 1, wherein the compound is labeled with $^{203}$Pb.
4. The compound of claim 1, wherein the compound is labeled with $^{212}$Pb.
* * * * *